(12) United States Patent
Lina et al.

(10) Patent No.: US 7,903,864 B1
(45) Date of Patent: Mar. 8, 2011

(54) SYSTEM AND METHODS FOR THE DETECTION OF IRREGULARITIES IN OBJECTS BASED ON AN IMAGE OF THE OBJECT

(75) Inventors: Arnaud Lina, Montreal (CA); Louis-Antoine Blais-Morin, Montreal (CA); Yves Rioux, Montréal (CA)

(73) Assignee: Matrox Electronic Systems, Ltd., Dorval, Quebec (CA)

( * ) Notice: Subject to any disclaimer, the term of this patent is extended or adjusted under 35 U.S.C. 154(b) by 937 days.

(21) Appl. No.: 11/624,213

(22) Filed: Jan. 17, 2007

(51) Int. Cl.
*G06K 9/00* (2006.01)
(52) U.S. Cl. .......................... 382/141; 382/149
(58) Field of Classification Search .................. 382/132, 382/141, 145, 149; 348/125
See application file for complete search history.

(56) References Cited

U.S. PATENT DOCUMENTS

| | | | | |
|---|---|---|---|---|
| 5,015,097 A | * | 5/1991 | Nomoto et al. | 356/314 |
| 5,493,594 A | * | 2/1996 | Hamada et al. | 378/34 |
| 5,526,119 A | * | 6/1996 | Blit et al. | 356/402 |
| 5,930,382 A | * | 7/1999 | Irie et al. | 382/147 |
| 6,330,354 B1 | * | 12/2001 | Companion et al. | 382/150 |
| 7,327,448 B2 | * | 2/2008 | Klein et al. | 356/237.1 |

OTHER PUBLICATIONS

Atsushi Teramoto, et al., Development of an Automated X-Ray Inspection Method for Microsolder Bumps; 2005 International Symposium on Electronic Materials and Packaging (EMAP2005), Dec. 11-14, 2005; pp. 21-26, Tokyo Institute of Technology, Tokyo, Japan.

* cited by examiner

*Primary Examiner* — Daniel G Mariam
(74) *Attorney, Agent, or Firm* — Foley & Lardner LLP

(57) ABSTRACT

A method for the detection of an irregularity in an object based on an image of the object that includes the steps of binarizing the image at a plurality of binarization thresholds to obtain a plurality of binarized images, extracting information from each of the binarized images, estimating the regular object resulting from the binarization at the respective binarization threshold of an image of a version of the object in which the irregularity is absent, combining the information extracted from each of the binarized images, and detecting the irregularity based on the combined information. A method for the detection of a defect in a solder element based on an X-ray image of the solder element. This aspect includes the steps of binarizing the image at a plurality of binarization thresholds to obtain a plurality of binarized images, extracting information from each of the binarized images, combining the information extracted from each of the binarized images, and detecting the defect based on the combined information.

27 Claims, 15 Drawing Sheets

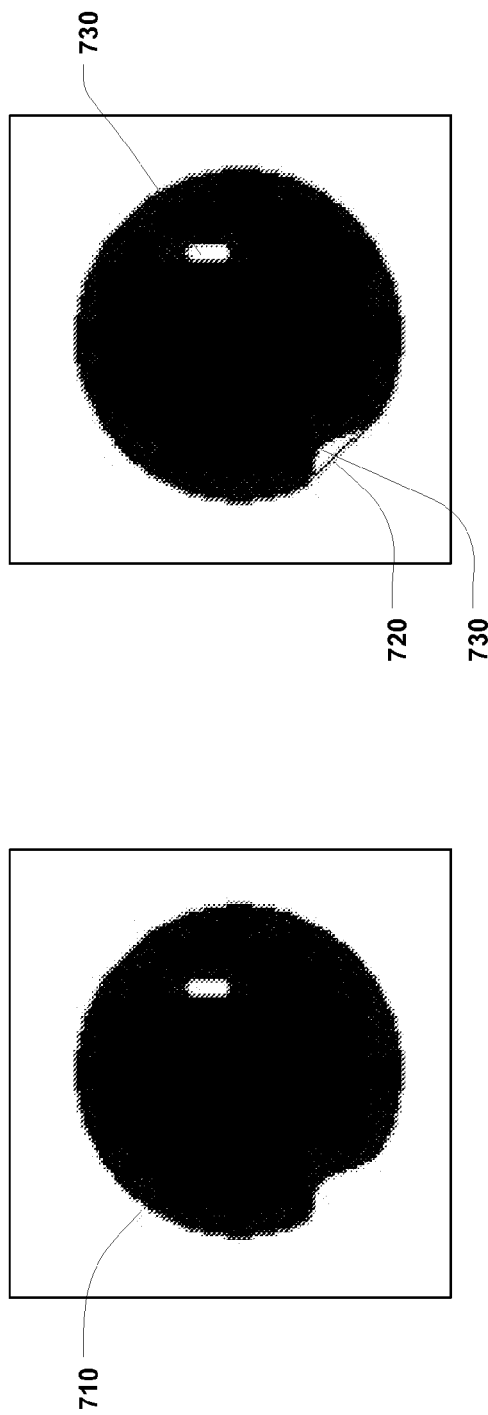
FIG. 7A
FIG. 7B
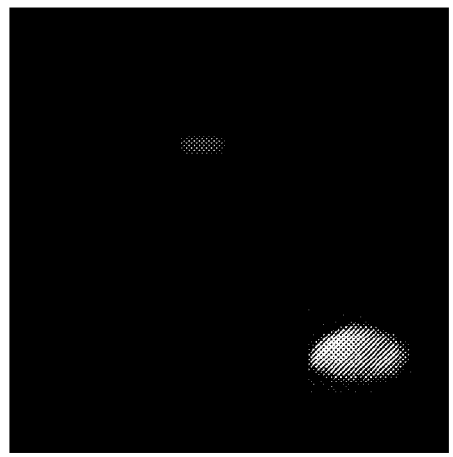
FIG. 7C
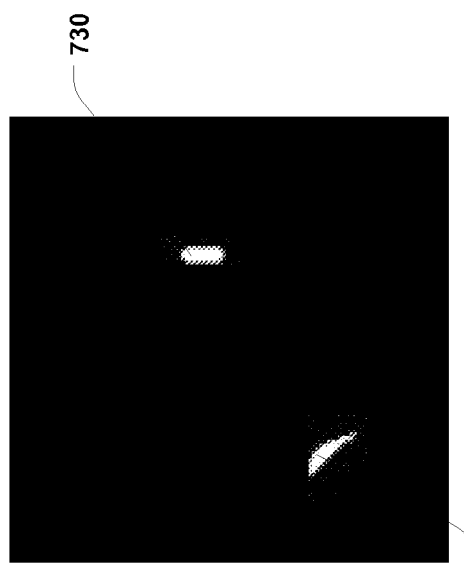
FIG. 7D

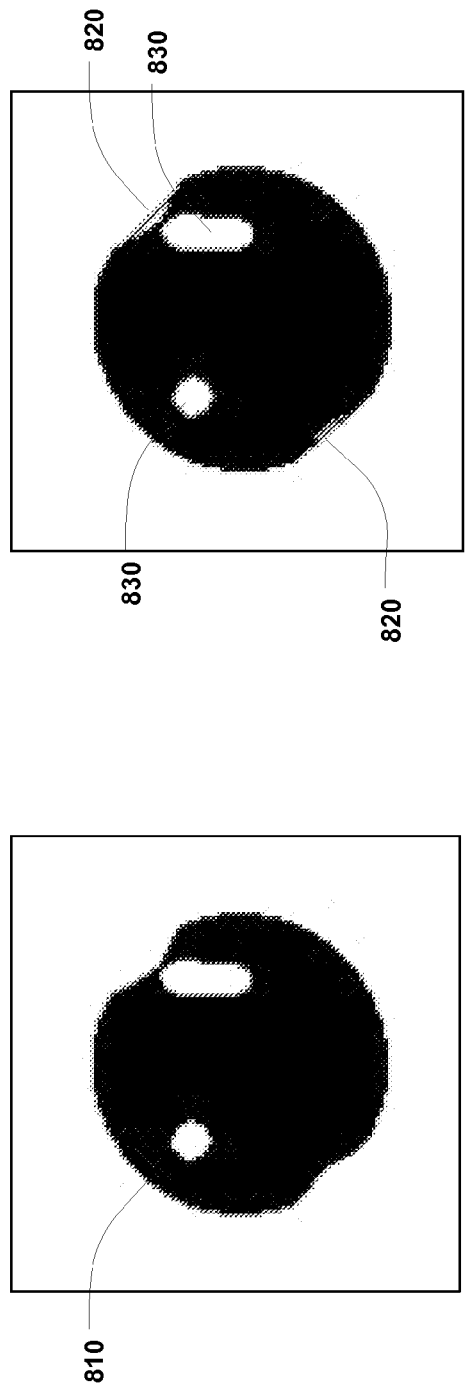
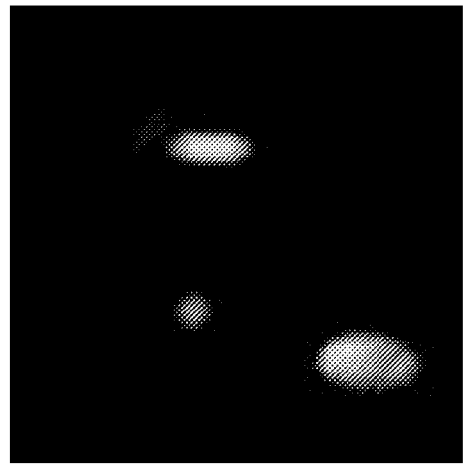
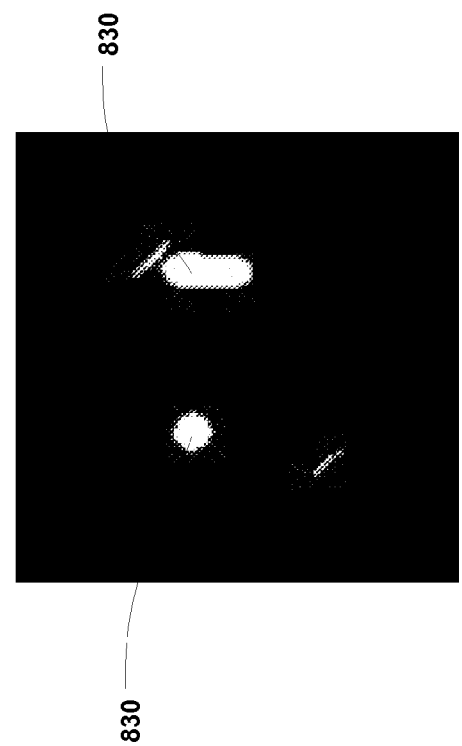
FIG. 8B
FIG. 8D
FIG. 8A
FIG. 8C

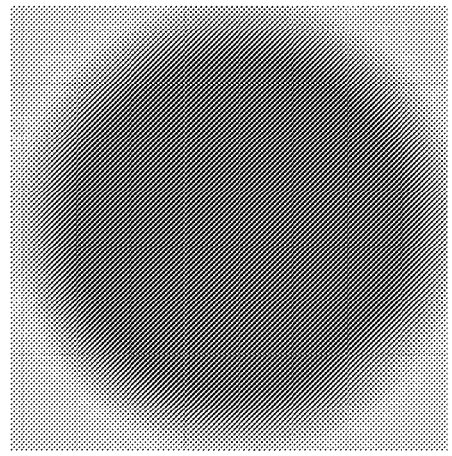
FIG. 12B
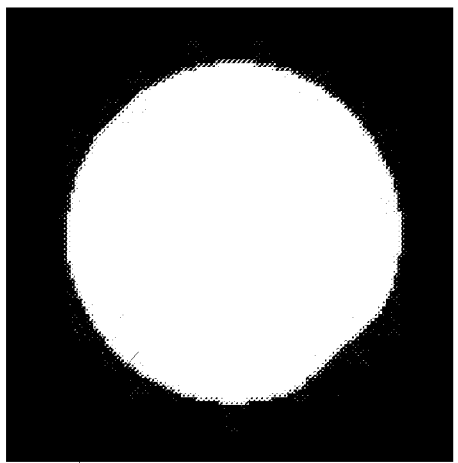
FIG. 12D
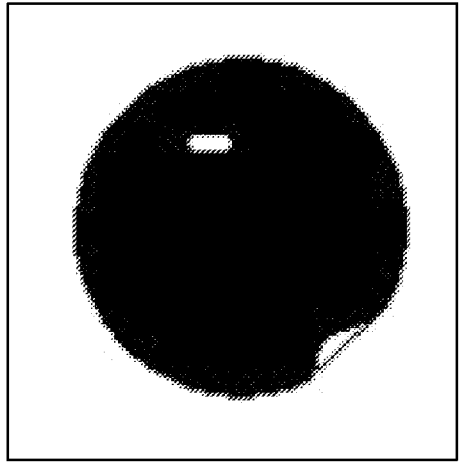
FIG. 12A
FIG. 12C
1230

US 7,903,864 B1

SYSTEM AND METHODS FOR THE DETECTION OF IRREGULARITIES IN OBJECTS BASED ON AN IMAGE OF THE OBJECT

BACKGROUND OF INVENTION

1. Field of Invention

This invention concerns methods for the detection of an irregularity in an object based on an image of the object. One embodiment is related generally to systems and methods for the detection of a defect in a solder element based on an X-ray image of the solder element.

2. Discussion of Related Art

Surface mount technology ("SMT") is an electronic circuit assembly process in which surface-mount devices, components, or parts, such as resistors, capacitors, integrated circuit packages, and the like, are soldered onto the surface of a printed circuit board ("PCB"). This differs from "leaded" or "through-hole" technology, in which leads of the device are inserted into holes in the PCB.

Among the variety of existing surface-mount packages for integrated circuits ("ICs") is the Ball Grid Array ("BGA"). While other surface-mount IC packages have pins extending from the sides of the package (e.g., the Dual In-line Package and the Quad Flat Package), BGA packages employ an array of spheres or balls of solder attached to the bottom surface of the package as external electrical interconnects. The solder balls can lie over all or a portion of the bottom surface of the package.

To assemble the BGA package on a printed circuit board, the BGA solder balls are first placed on corresponding solder pads on the PCB surface, such as by use of a pick-and-place machine. The PCB is then placed in a reflow oven, in which the solder balls are caused to melt. The solder balls then cool and solidify, soldering the BGA package to the PCB.

A common defect in BGA solder balls is the presence of bubbles of gas, known as voids, in the solder. Depending on the quantity of voids in the solder ball, their size relative to the size of the solder ball, and their location in the solder ball, voids can affect the quality and/or reliability of the resulting solder joints. In order to ensure the quality of the solder joints, therefore, it is necessary to inspect solder balls to detect occurrences of voids and measure their characteristics. Characteristics of interest may include position, diameter, depth, area, volume, and the like.

Due to the fact that they are hidden below the surface of the solder ball, voids cannot be detected by visual or optical inspection. For this reason, X-ray imaging may be used to inspect solder balls for voids.

SUMMARY OF THE INVENTION

One aspect of the invention provides a method for the detection of an irregularity in an object based on an image of the object. In this aspect, the method includes the steps of binarizing the image at a plurality of binarization thresholds to obtain a plurality of binarized images, extracting information from each of the binarized images, estimating the regular object resulting from the binarization at the respective binarization threshold of an image of a version of the object in which the irregularity is absent, combining the information extracted from each of the binarized images, and detecting the irregularity based on the combined information.

This first aspect of the invention may further include the additional step of estimating the non-defective solder element resulting from the binarization, at the respective binarization threshold, of an X-ray image of a version of the solder element in which the defect is absent.

Another aspect of the invention provides a method for the detection of a defect in a solder element based on an X-ray image of the solder element. This aspect includes the steps of binarizing the image at a plurality of binarization thresholds to obtain a plurality of binarized images, extracting information from each of the binarized images, combining the information extracted from each of the binarized images, and detecting the defect based on the combined information.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 7A is an representative image resulting from the thresholding step in a second iteration of the embodiment reflected in FIG. 5;

FIG. 7B is an representative image of a convex envelope in a second iteration the embodiment reflected in FIG. 5;

FIG. 7C is an image representative of inner blobs obtained in a second iteration of the embodiment reflected in FIG. 5;

FIG. 7D is an image representative the accumulation obtained in a second iteration of the embodiment reflected in FIG. 5;

FIG. 8A is an representative image resulting from the thresholding step in a third iteration of the embodiment reflected in FIG. 5;

FIG. 8B is an representative image of a convex envelope in a third iteration the embodiment reflected in FIG. 5;

FIG. 8C is an image representative of inner blobs obtained in a third iteration of the embodiment reflected in FIG. 5;

FIG. 8D is an image representative the accumulation obtained in a third iteration of the embodiment reflected in FIG. 5;

FIG. 12A is an representative image resulting from the thresholding step in a second iteration of the embodiment reflected in FIG. 10;

FIG. 12B is an representative image of a convex envelope in a second iteration the embodiment reflected in FIG. 10;

FIG. 12C is an image representative of inner blobs obtained in a second iteration of the embodiment reflected in FIG. 10;

FIG. 12D is an image representative the accumulation obtained in a second iteration of the embodiment reflected in FIG. 10;

DETAILED DESCRIPTION

Figure 1A:
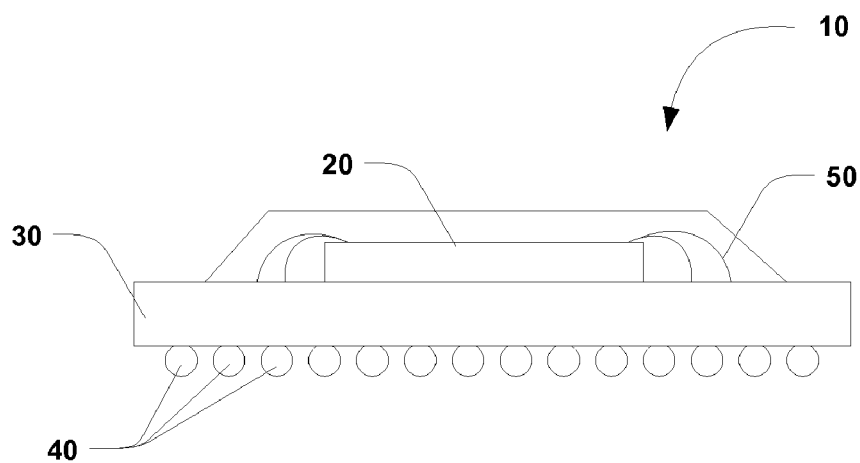
FIG. 1A is a side view of an exemplar BGA package.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof, is meant to encompass the items listed thereafter and equivalents thereof as well as additional items.

In one embodiment, the present method addresses the problem of accurately detecting and/or characterizing the occurrences of voids in materials. As used herein, "characterizing" means determining physical characteristics of a void, such as, but not limited to, the position, diameter, depth, area, volume, etc. of the void.

The invention is described below in the context of detecting and characterizing voids in BGA solder balls. As will be discussed, however, the method is not limited to BGA solder balls, solder, or any other specific material, and it may be extended to various other applications.

Figure 1B:
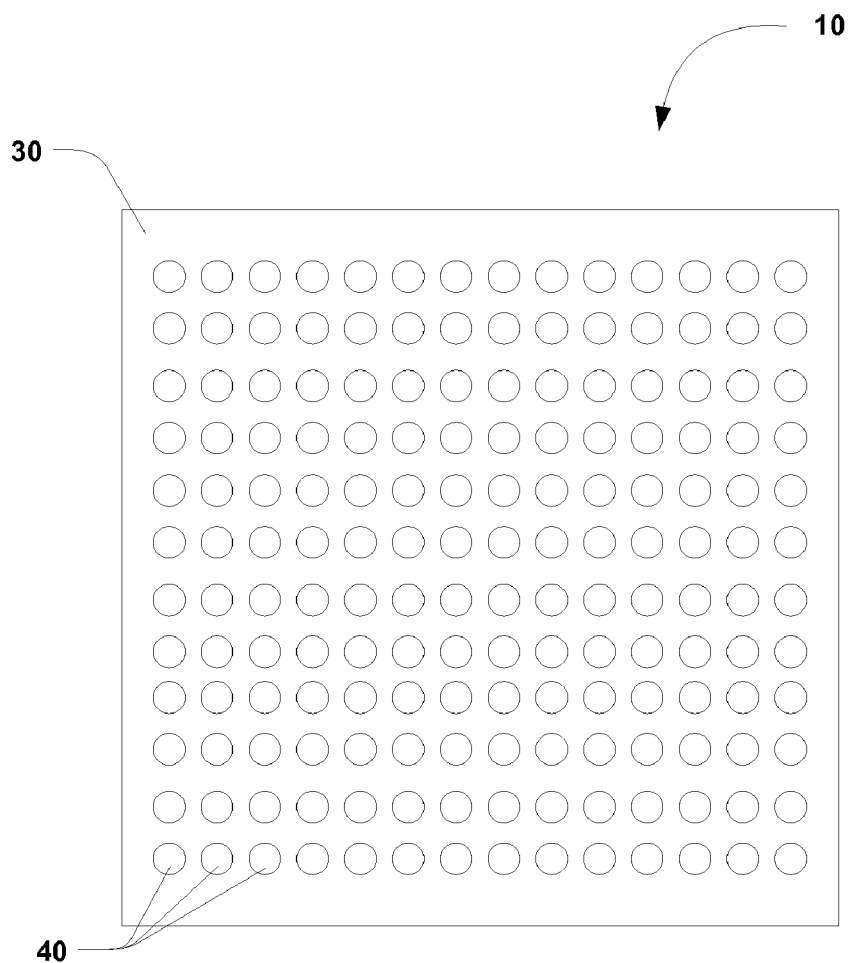
FIG. 1B is a bottom view of the BGA package of FIG. 1A.

FIGS. 1A-1B depict side and bottom views, respectively, of an exemplar BGA package 10 prior to mounting on a PCB. The package 10 includes a die 20 bonded to a substrate 30 to which are attached a number of solder balls 40. In the illustrated BGA package 10, the die 20 is bonded to the substrate 30 via wire bonds 50.

Figure 2:
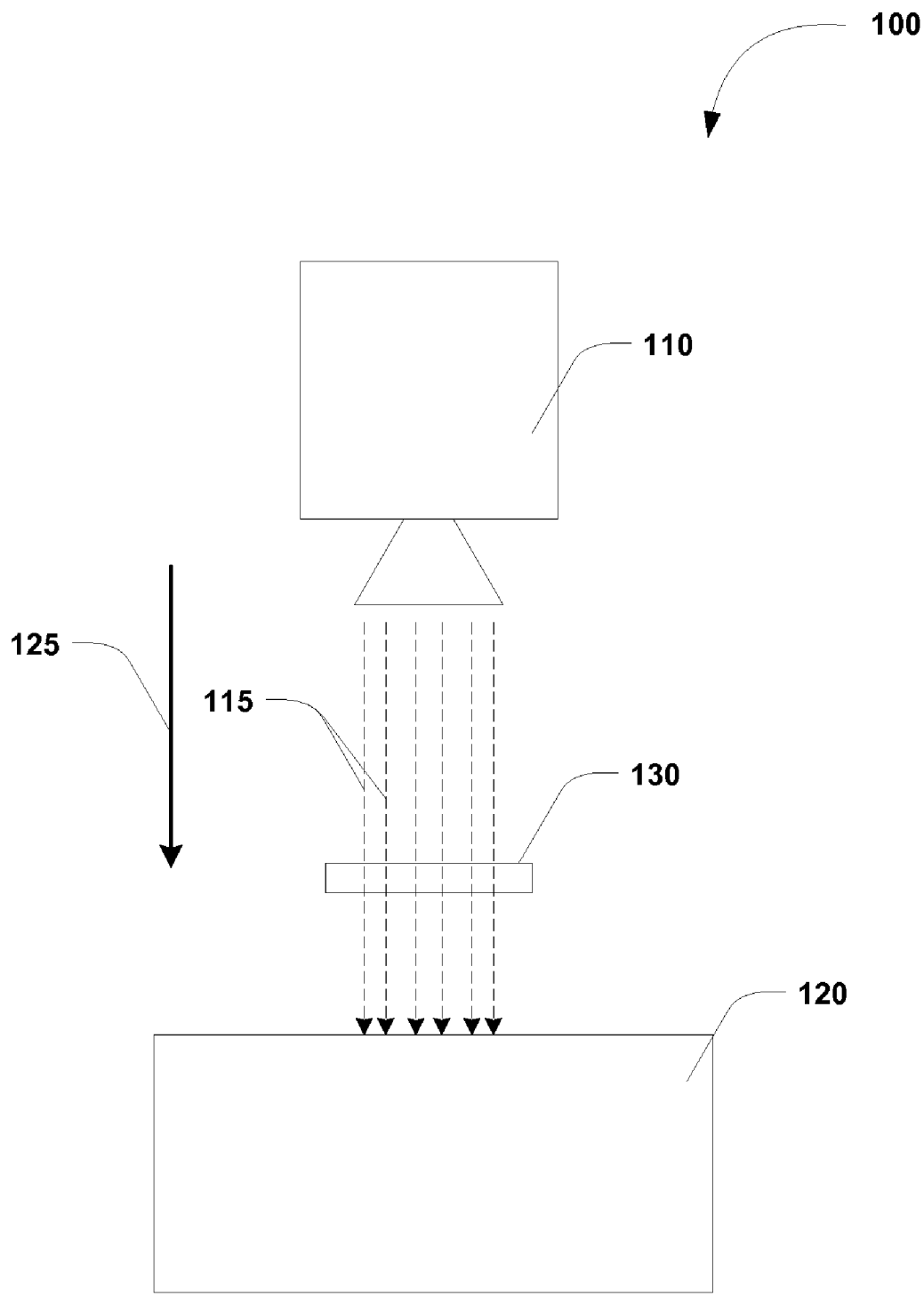
FIG. 2 is a schematic drawing of an exemplar X-ray inspection station.

As shown schematically in FIG. 2, an X-ray imaging system 100 suitable for use with the invention may include an X-ray source 110 and an X-ray detector 120 placed on either side of a sample 130, such as the BGA package 10 shown in FIG. 1, under inspection. The X-ray source 110 may emit X-rays 115 that travel through the sample 130 and are then collected by the X-ray detector 120. The amount of X-rays 115 that exit the sample 130 for collection by the X-ray detector 120 is a function of the thickness of the sample 130 and of the X-ray absorption properties of the materials composing the sample.

In the case of the inspection of a BGA package, the package may be placed right side up (with the solder balls facing downward) or upside down (with the solder balls facing upwards) relative to the X-ray source 110. The viewing direction 125 is typically perpendicular to the top and bottom surfaces of the BGA package, but this is not a requirement.

In a digital X-ray system, the X-ray detector 120 generates a grayscale image of the sample, in which the brightness or grayscale intensity of a pixel is a function of the thickness and the coefficient of absorption of the sample along the corresponding X-ray path. In some cases, an 8-bit grayscale intensity format may be employed, such that the "darkest" pixel is represented by a grayscale intensity of 0 and the "brightest" pixel is represented by a grayscale intensity of 255.

Figure 3:
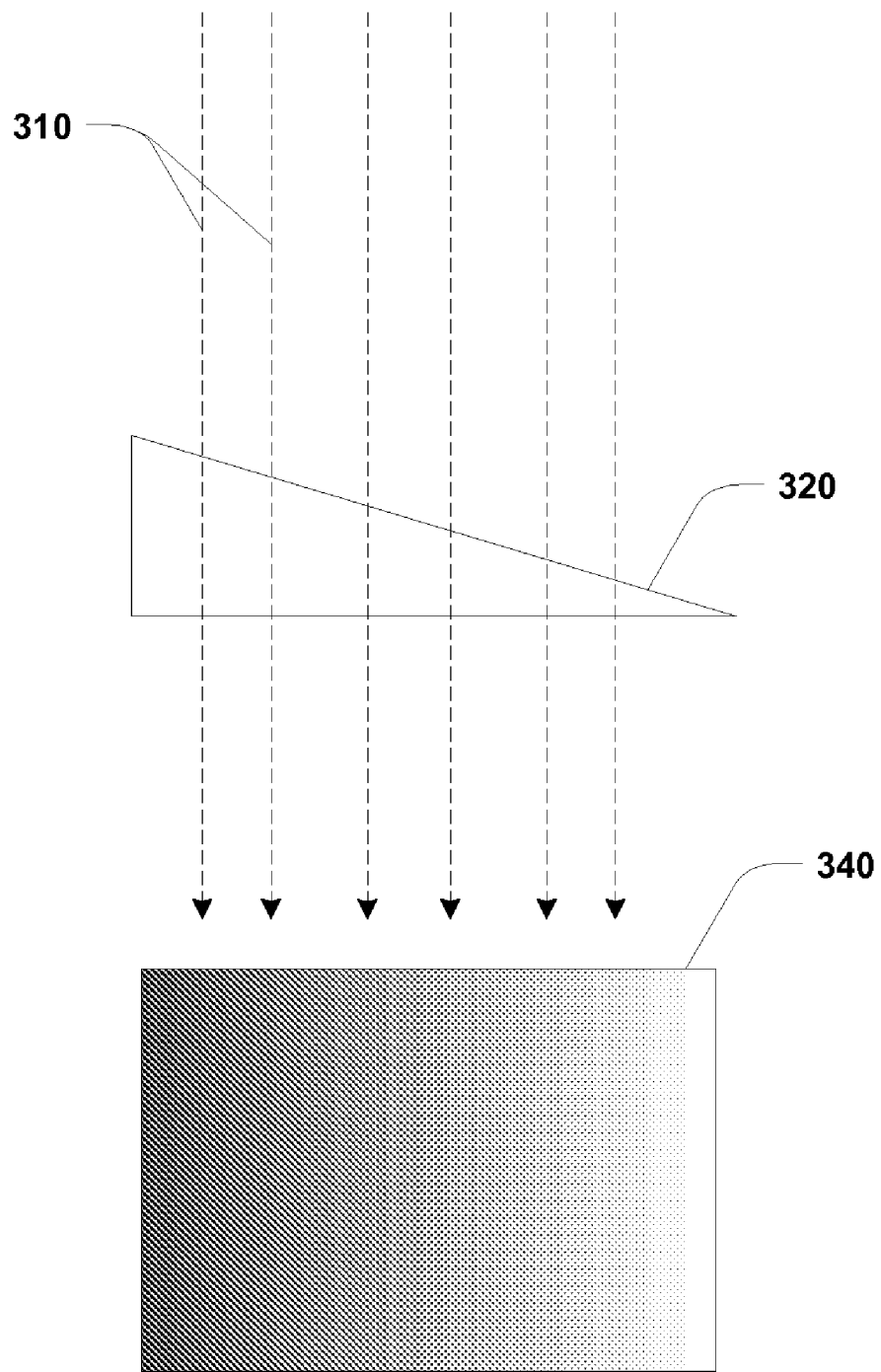
FIG. 3 is a schematic drawing illustrating an X-ray sample and a grayscale image generated from the sample.

In one embodiment, the thicker the sample, or the higher its absorption coefficient along the X-ray path, the darker the corresponding pixel in the resulting grayscale X-ray image (i.e., the lower the grayscale intensity of the pixel). In the example shown in FIG. 3, the portions of the image 340 that are darker indicate portions of the sample 320 that are "thicker," while the portions of the image 340 that are lighter shades correspond to portions of the sample 320 that are "thinner." Thicker or thinner in this context refers to relative amounts of material lying in the paths of the X-rays 310 corresponding to a given pixel in the image.

Figure 4:
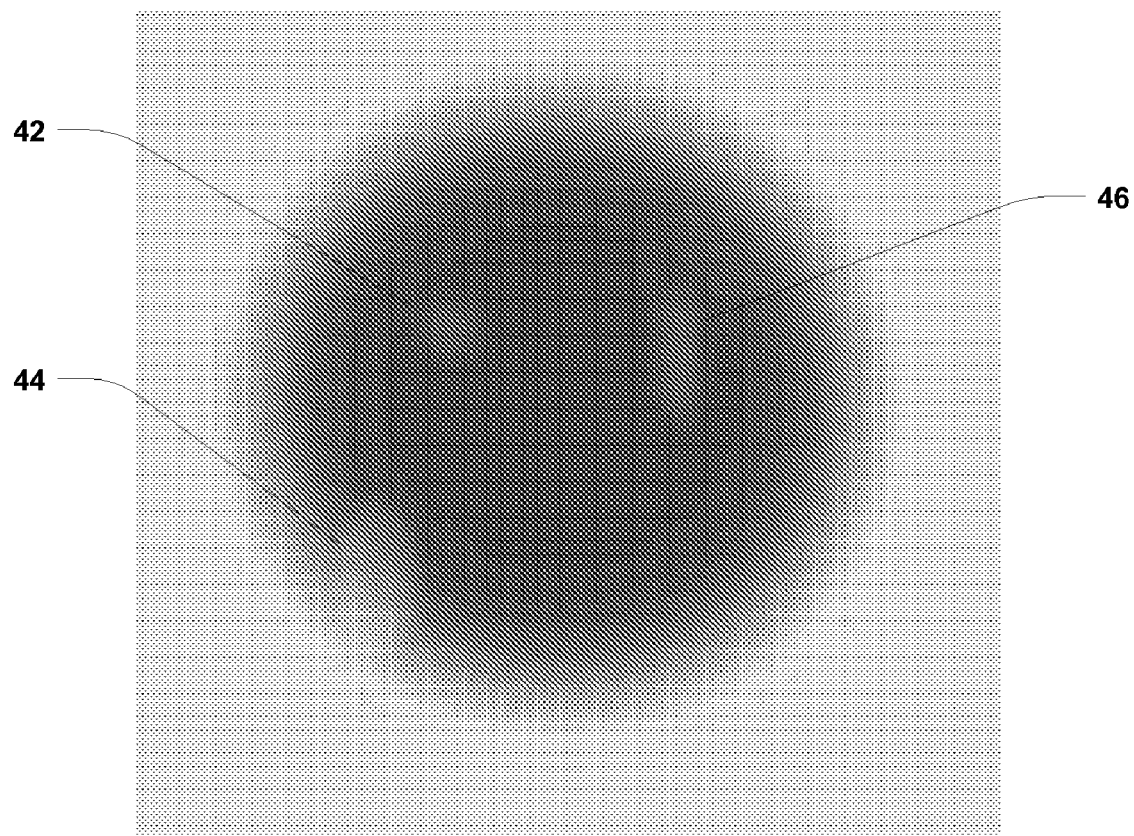
FIG. 4 is a mock-up of an X-ray image of a BGA solder ball.

FIG. 4 shows an exemplary grayscale X-ray image of a single solder ball 40. The X-ray image of FIG. 4 may be, for example, a portion of a larger X-ray image of an entire BGA package generated by the above-described X-ray imaging system. As can be seen in FIG. 4, the image exhibits generally elliptical regions of pixels of slightly higher grayscale intensity than the surrounding pixels. Examples of these elliptical regions are indicated by reference numerals 42, 44, and 46. These lighter regions 42, 44, and 46 correspond to voids in the imaged solder ball.

The presence of one or more voids (bubbles of gas replacing what should be solder) along an X-ray path means a smaller effective thickness of solder along the X-ray path and therefore results in a higher (lighter) grayscale intensity at the corresponding pixel in the X-ray image. Furthermore, the contrast between the void region and the surrounding area is a useful measure of the importance of the void(s) in the viewing direction relative to that of the solder ball.

In general, voids in solder balls may be difficult to accurately detect and characterize due to the very small contrast between the void regions and their surrounding area, the non-uniform grayscale intensity over the area of the solder ball, the fact that the exact geometry/shape of the solder ball is unknown, and the noisy nature of X-ray imaging. All of these factors make it difficult to find a binarization threshold that will isolate all the voids. The generally spherical shape of the solder ball means that the thickness of the solder ball is highest at the center of the solder ball and decreases in a radial direction towards the inner boundary of the solder ball. Thus, in the grayscale X-ray image of the solder ball (e.g., FIG. 4), the grayscale intensity of the pixels increases (i.e., the pixels become lighter) radially towards the inner boundary of the solder ball. For various reasons, in practice, this is only apparent near the boundaries of the solder ball.

Figure 5:
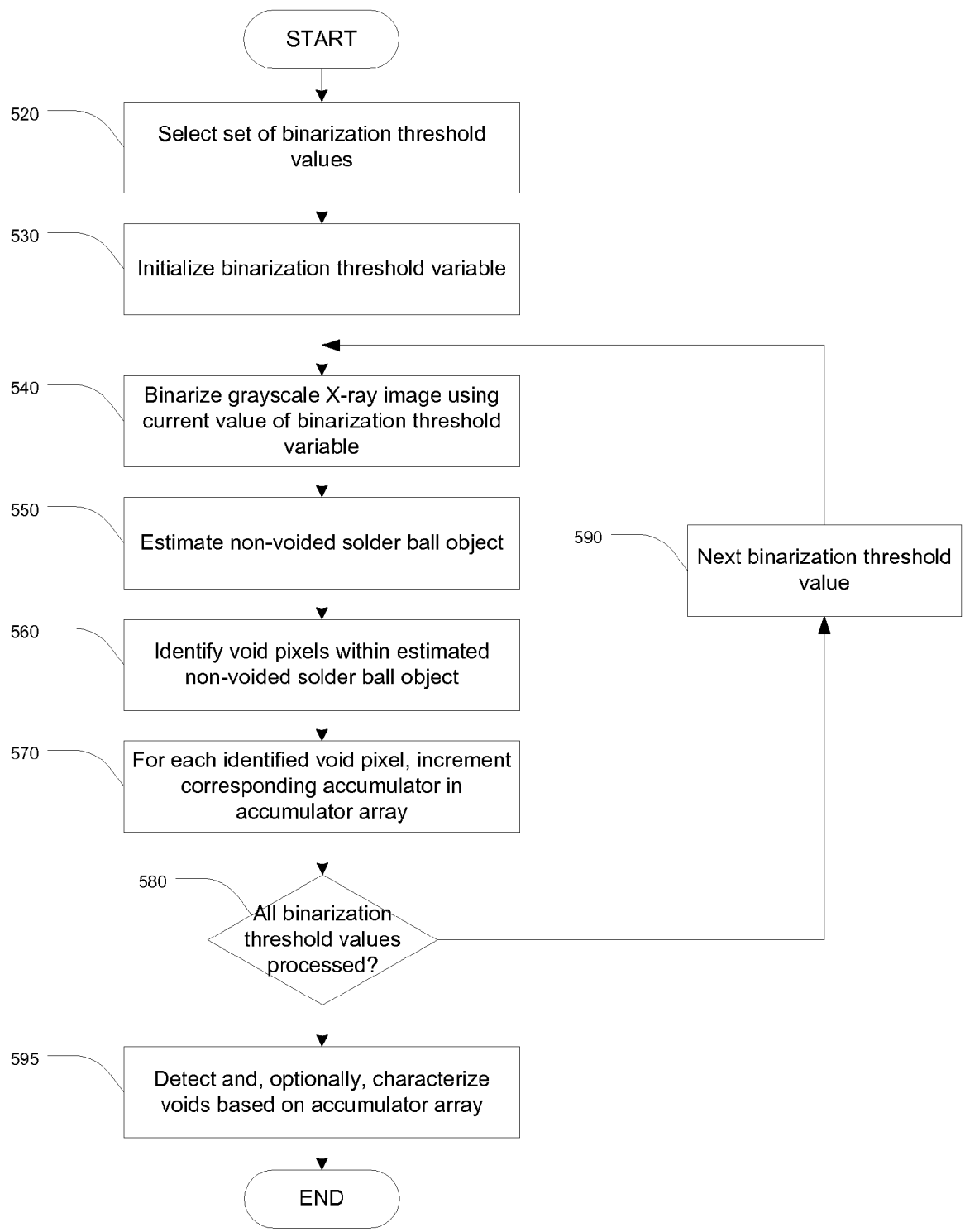
FIG. 5 is a flowchart illustrating steps associated with one embodiment of the invention.

FIG. 5 describes the steps of an embodiment of the invention relating to the detection of voids in a solder ball. This illustrative embodiment begins with a grayscale X-ray image of a single solder ball, such as that of FIG. 4.

At step 520, an appropriate set of binarization threshold values, with which to successively binarize the grayscale X-ray image, is selected. The set of binarization threshold values can be represented, for example, as a combination of a range [Tmin, Tmax] and a step size ΔT.

In some embodiments, the range of binarization threshold values [Tmin, Tmax] is selected based on the grayscale intensity values of the set of pixels in the grayscale X-ray image corresponding to the solder ball. For example, the lowest and highest grayscale intensity values among the set of solder ball pixels can be selected as the minimum binarization threshold value, Tmin, and the maximum binarization threshold value, Tmax, respectively. The set of pixels in the grayscale X-ray image corresponding to the solder ball can be determined, for example, by binarizing the grayscale X-ray image and locating in the binarized image a group ("blob") of pixels having the same binary intensity.

Preferably, the step size, ΔT, should be small enough that no significant void information is missed. In some embodiments, the step size may be selected based on the desired or required precision and processing speed. For example, if the contrast between the void region(s) and the surrounding area is small, a smaller step size should be selected. Of course, a smaller step size will increase the degree of processing required. In some embodiments, the user may select the step size. For example, the user may be given the option to choose between a step size of 1 and a step size of 3; using a step size of 1, every single grayscale intensity value within the range [Tmin, Tmax] is selected.

At step 530, a binarization threshold variable is initialized to the maximum binarization threshold value, Tmax. According to the present embodiment, at each iteration of the loop, the binarization threshold variable is decremented according to the step size, ΔT, until the minimum binarization threshold value, Tmin, has been processed. It should be understood, however, that the binarization threshold values can be processed in any order.

At step 540, the grayscale X-ray image of the solder ball is binarized using the current value of the binarization threshold variable. In one embodiment, this consists of setting all pixels having a grayscale intensity value larger than the binarization threshold to white in the binarized image, while setting the remaining pixels to black.

Figure 6A:
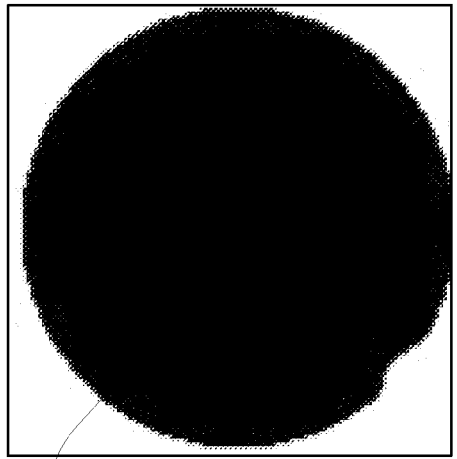
FIG. 6A is an representative image resulting from the thresholding step in a first iteration of the embodiment reflected in FIG. 5.
Figure 6B:
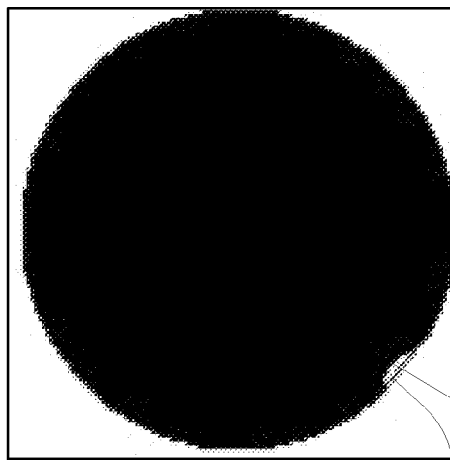
FIG. 6B is an representative image of a convex envelope in a first iteration the embodiment reflected in FIG. 5.
Figure 6C:
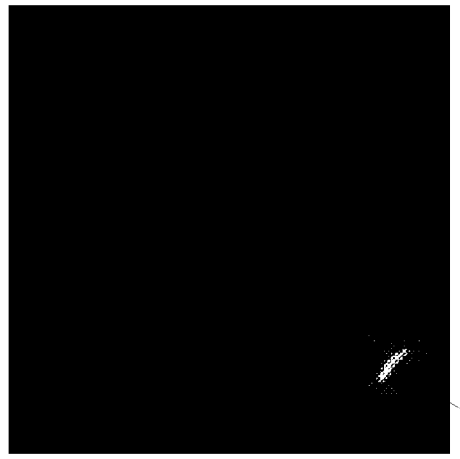
FIG. 6C is an image representative of inner blobs obtained in a first iteration of the embodiment reflected in FIG. 5.
Figure 6D:
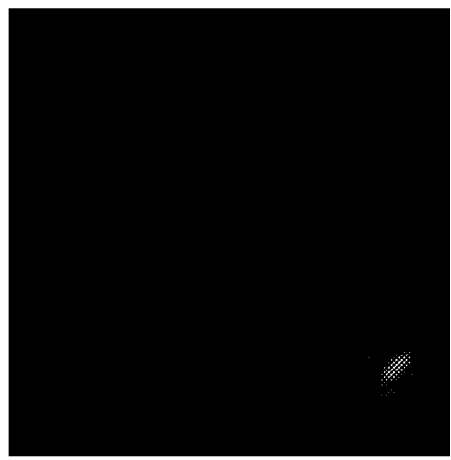
FIG. 6D is an image representative the accumulation obtained in a first iteration of the embodiment reflected in FIG. 5.

FIG. 6A illustrates the binary image obtained by binarizing the grayscale X-ray image of FIG. 4 at a particular binarization threshold value, i.e., during a particular iteration of the loop.

Because the grayscale intensity of the pixels forming the solder ball in the grayscale X-ray image increases as you move radially outward toward the boundary of the solder ball, the solder ball appears in an "eroded" form (with a smaller radius) in the binarized image.

Figure 9B:
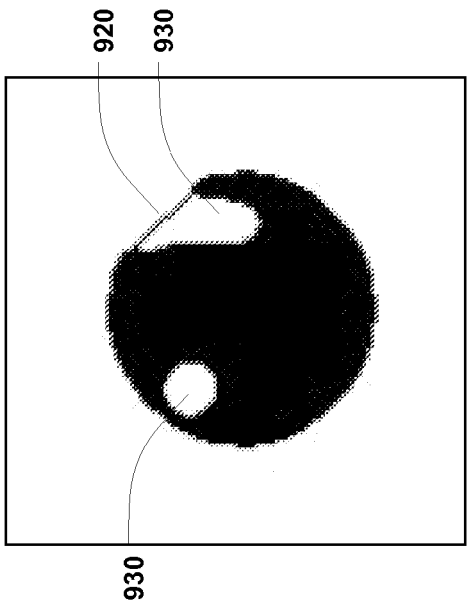
FIG. 9B is an representative image of a convex envelope in a fourth iteration the embodiment reflected in FIG. 5.
Figure 9D:
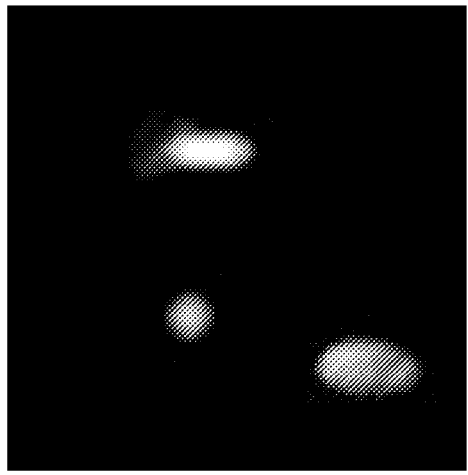
FIG. 9D is an image representative the accumulation obtained in a fourth iteration of the embodiment reflected in FIG. 5.
Figure 9A:
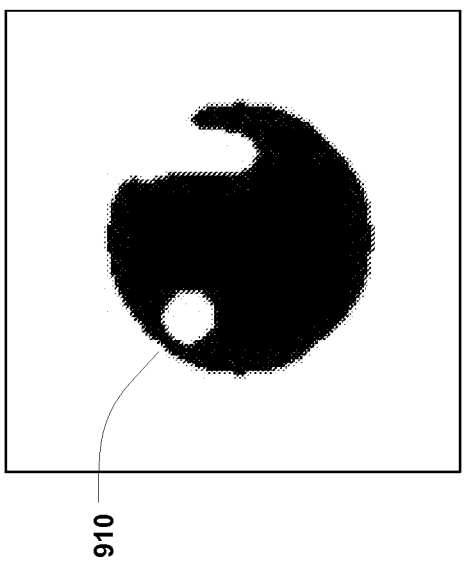
FIG. 9A is an representative image resulting from the thresholding step in a fourth iteration of the embodiment reflected in FIG. 5.
Figure 9C:
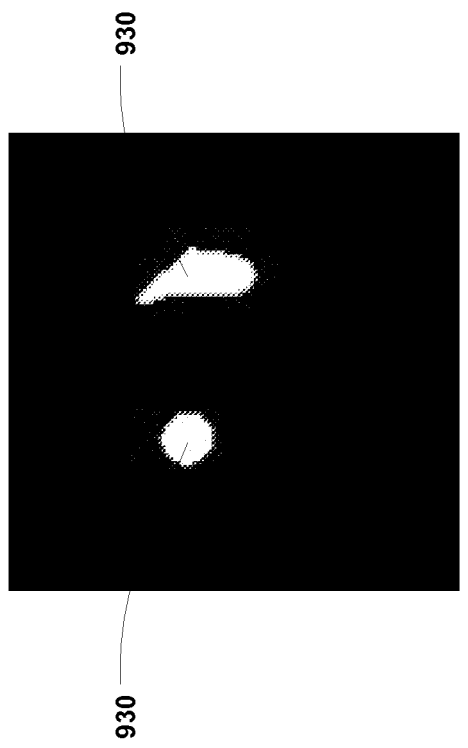
FIG. 9C is an image representative of inner blobs obtained in a fourth iteration of the embodiment reflected in FIG. 5.

FIGS. 7A, 8A, and 9A illustrate the binarized images obtained at step 540 during subsequent iterations of the loop, i.e., for decreasing binarization threshold values. As the binarization threshold is decreased at each iteration of the loop, the solder ball appears increasingly eroded (with a smaller and smaller radius), in the binarized X-ray images, until the shape of the solder ball is completely lost (not shown).

Step 550 estimates the non-voided solder ball object that would result from binarizing, at the current value of the binarization threshold variable, a grayscale X-ray image of a version of the solder ball in which the voids are absent.

In one embodiment, step 550 is achieved by identifying the voided solder ball object in the binarized image and determining the convex envelope of the identified voided solder ball object. The convex envelope of an object can be thought of as the boundary an elastic band stretched around the object would define. A number of methods are known in the art to determine the convex envelope of a set of points. In FIGS. 6A-B, 7A-B, 8A-B, and 9A-B, the voided solder ball objects are indicated by reference numerals 610, 710, 810, and 910, respectively, and their convex envelopes are indicated by reference numerals 620, 720, 820, and 920, respectively.

In another embodiment (not shown), step 550 may be achieved by identifying a set of points belonging to the boundary of the voided solder ball object and fitting a pre-defined geometric shape to the set of boundary points. The pre-defined shape may be, but is not limited to, any one of a circle, ellipse, paraboloid, etc. In one embodiment, fitting a pre-defined geometric shape to a set of points consists of determining the parameters of the pre-defined shape that best fits the set of points. A number of methods are known in the art to accomplish the fitting operation.

In other embodiments, the step 550 of estimating the regular object may be performed using any of a number of geometric properties of the voided solder ball object and/or the set of boundary points. Such properties may include convexity, concavity, dimensions such as a length or width, the area, centers of gravity, or circumscribed, inscribed, or fitted shapes, such as but not limited to one or more circles, ellipses, paraboloids, and polygons.

At step 560, the pixels corresponding to a void ("void pixels") within the estimated non-voided solder ball object determined at step 550 are identified. For example, in the embodiment illustrated in FIGS. 6B-C, all white pixels 630 inside the convex envelope 620 are identified. In FIGS. 7B-C, 8B-C, and 9B-C, the identified void pixels are indicated by reference numerals 730, 830, and 930, respectively. FIGS. 6C, 7C, 8C, and 9C illustrate binary images in which all identified void pixels are set to white and the remaining pixels are set to black.

At step 570, for each identified void pixel, the corresponding accumulator in an accumulator array is incremented. In one embodiment, the size of the accumulator array is equal to the size of the X-ray image, such that each pixel in the X-ray image has a corresponding accumulator in the array, in a one-to-one manner. In other embodiments, however, the accumulator array may be smaller than the X-ray image (i.e., several pixels are assigned to a single accumulator), although with a loss of precision.

In one embodiment, over several iterations of the loop, the value accumulated by an accumulator of the accumulator array is equal to the number of times the corresponding pixel in the binarized X-ray images was identified as a void pixel. The accumulator array may itself be viewed as a grayscale image, in which the grayscale intensity of a pixel corresponds to the number of times the corresponding pixel in the binarized X-ray image was identified as a void pixel. FIGS. 6D, 7D, 8D, and 9D illustrate the accumulator image obtained at step 570 for the different iterations of the loop.

At step 580, if there are still binarization threshold values that have not been processed, the method proceeds to step 590. At step 590, the binarization threshold variable is decremented according to the step size, ΔT. Steps 540 through 570 are then repeated using the new value of binarization threshold variable.

At step 595, once all binarization threshold values have been processed, the accumulator array or image is analyzed to detect the voids and, optionally, characterize the voids. As illustrated in FIGS. 6-9, each of the binarized images in FIGS. 6A, 7A, 8A, and 9A contributes different information, in the form of the void pixels 630, 730, 830, and 930, about the voids 42, 44, and 46 illustrated in FIG. 4. Once all binarization threshold values have been processed, the accumulator array or image provides comprehensive information regarding the voids 42, 44, and 46 that cannot be extracted from any one of the binarized images alone.

In some embodiments, step 595 may include a first step of filtering out noise from the accumulator image. As mentioned previously, in one embodiment, the grayscale intensity of a pixel in the accumulator image is equal to the number of times the corresponding pixel in the binarized images was identified as a void pixel. Accordingly, pixels in the accumulator image having relatively small grayscale intensities correspond to pixels that were identified as voids at relatively few binarization threshold values; these pixels are more likely to correspond to noise, than to significant voids. Therefore, in one embodiment, noise may be filtered out of the accumulator image and significant voids may be selected. First, only values in the accumulator image over an adequate threshold can be considered. For example, the threshold value may be selected to select voids which have a minimal corresponding thickness. Then, the selected values may be analyzed to form groups of connected pixels or blobs. These blobs can be further analyzed and discarded based on their size for example, or any other of their properties.

In the de-noised accumulator image, pixels having a non-zero grayscale intensity are assumed to belong to voids. Finally, if desired, characteristics of the voids can be determined from the de-noised accumulator image, such as position, diameter, depth, area, volume, etc.

Figure 15:
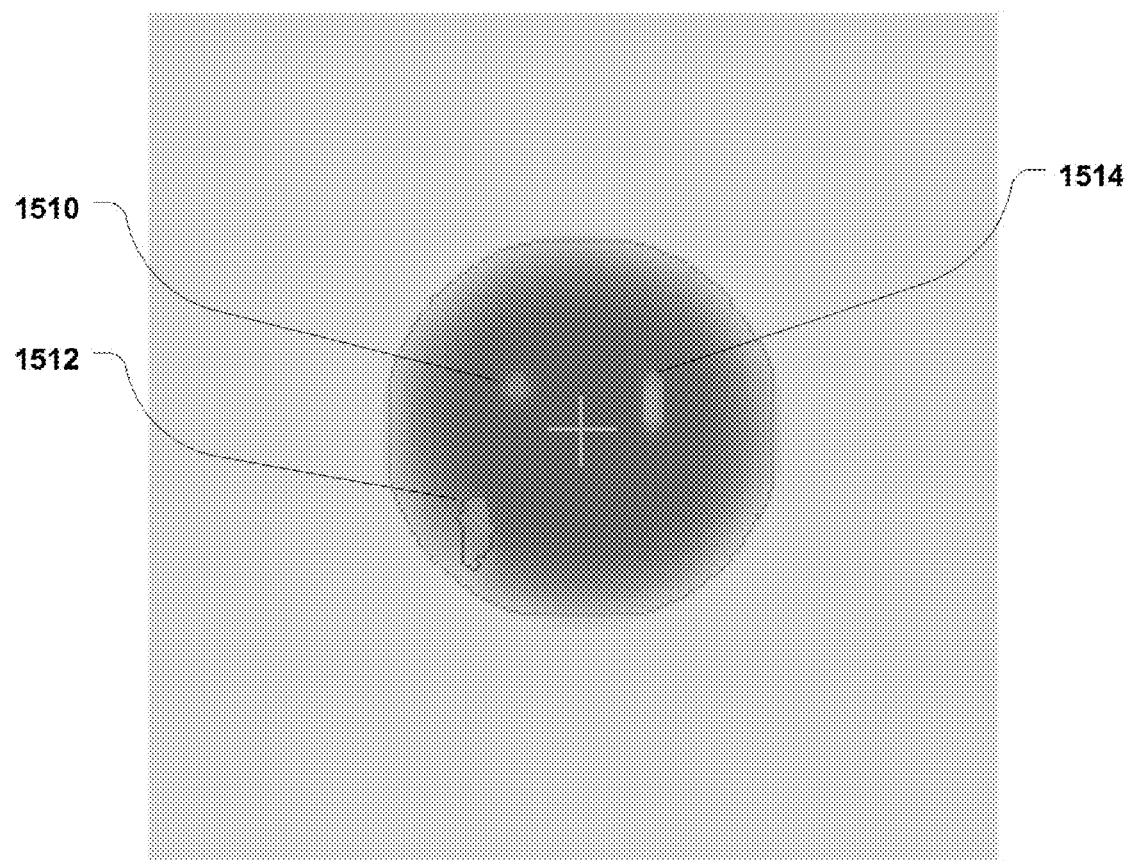
FIG. 15 illustrates the grayscale X-ray image of FIG. 4, in which the boundaries of blobs identified as voids have been identified.

FIG. 15 illustrates the grayscale X-ray image of FIG. 4, in which the boundaries 1510, 1512 and 1514 of blobs identified as voids according to step 595 have been identified.

Figure 10:
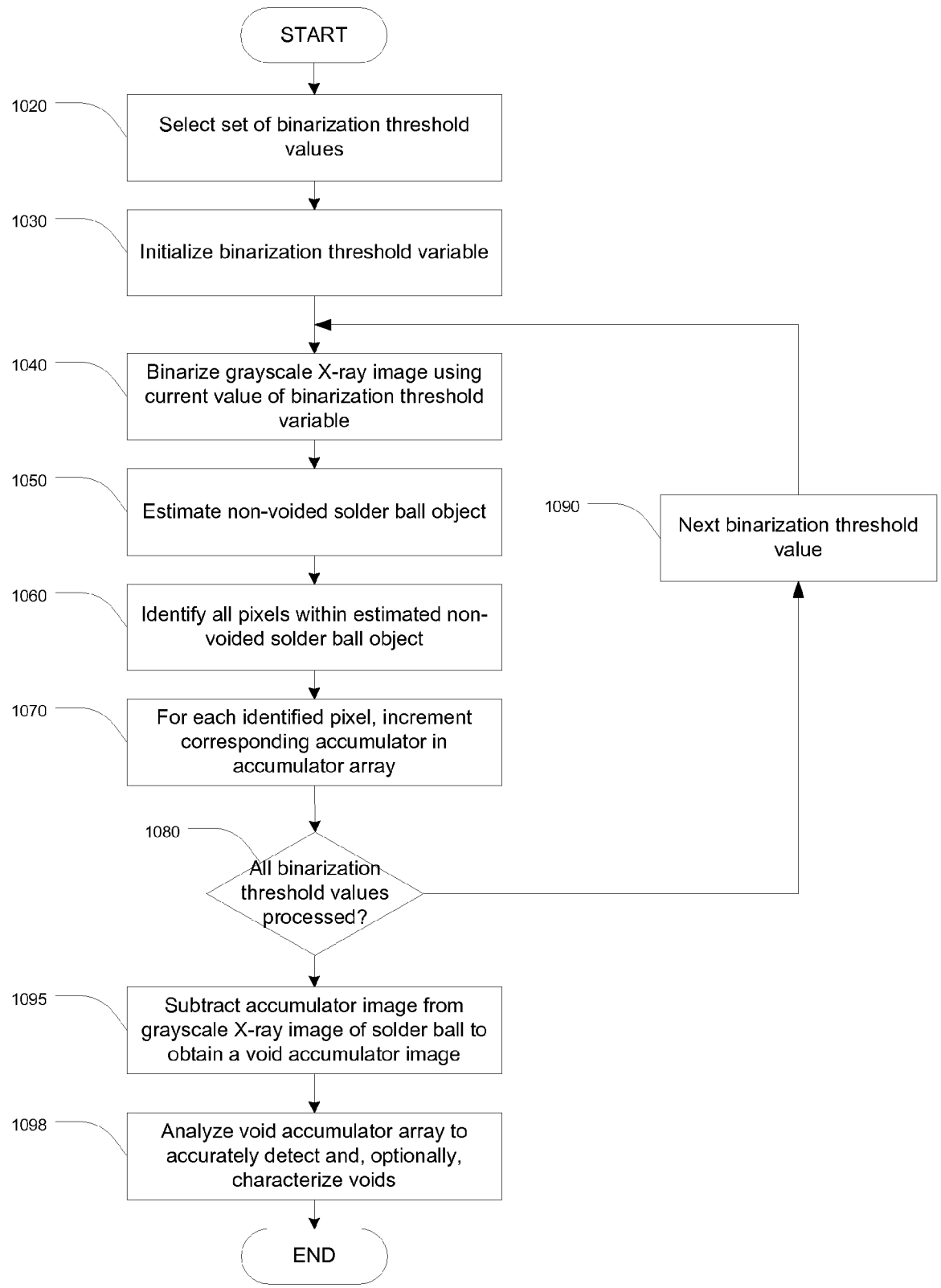
FIG. 10 is a flowchart illustrating steps associated with another embodiment of the invention.
Figure 11A:
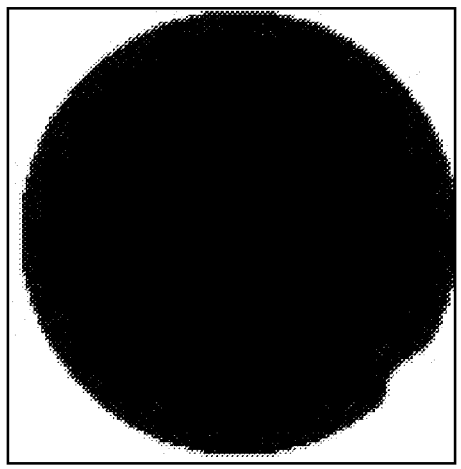
FIG. 11A is an representative image resulting from the thresholding step in a first iteration of the embodiment reflected in FIG. 10.
Figure 11B:
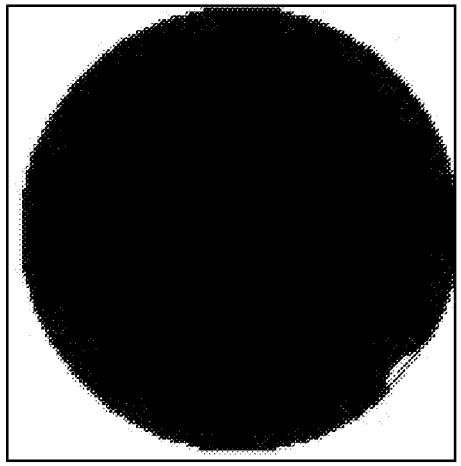
FIG. 11B is an representative image of a convex envelope in a first iteration the embodiment reflected in FIG. 10.
Figure 11C:
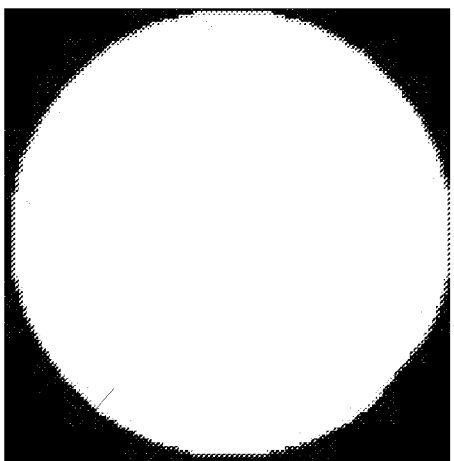
FIG. 11C is an image representative of inner blobs obtained in a first iteration of the embodiment reflected in FIG. 10.
Figure 11D:
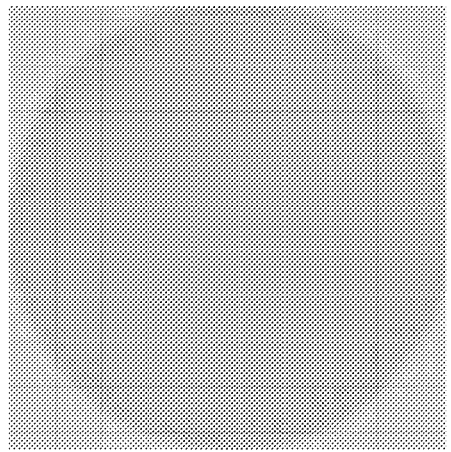
FIG. 11D is an image representative the accumulation obtained in a first iteration of the embodiment reflected in FIG. 10.
Figure 13B:
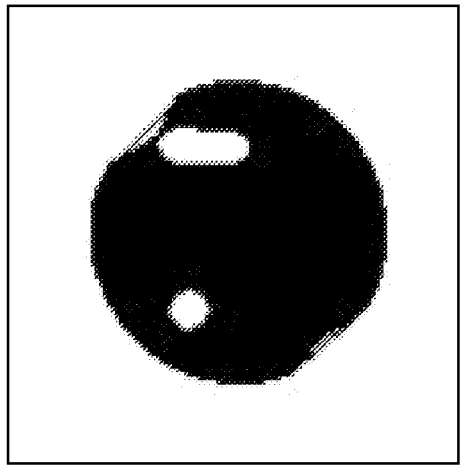
FIG. 13B is an representative image of a convex envelope in a third iteration the embodiment reflected in FIG. 10.
Figure 13D:
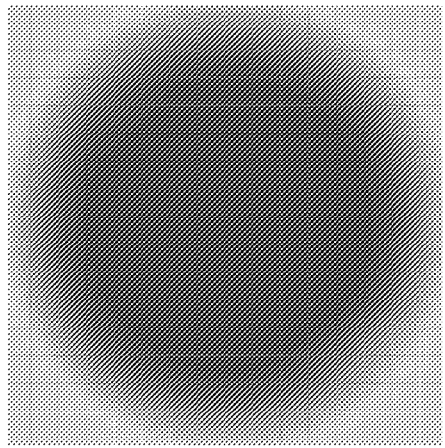
FIG. 13D is an image representative the accumulation obtained in a third iteration of the embodiment reflected in FIG. 10.
Figure 13A:
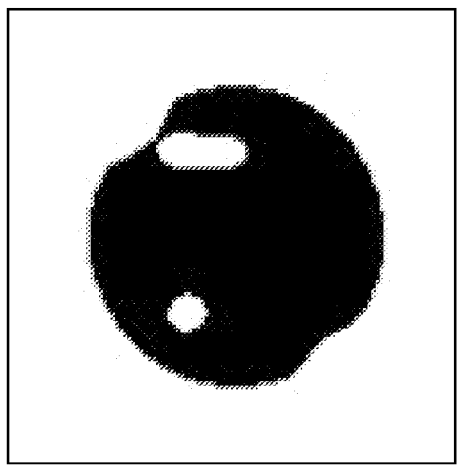
FIG. 13A is an representative image resulting from the thresholding step in a third iteration of the embodiment reflected in FIG. 10.
Figure 13C:
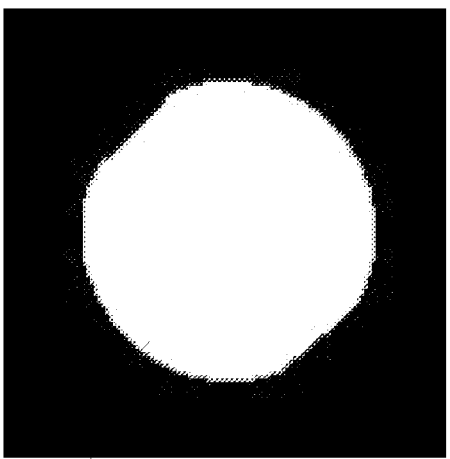
FIG. 13C is an image representative of inner blobs obtained in a third iteration of the embodiment reflected in FIG. 10.
Figure 14B:
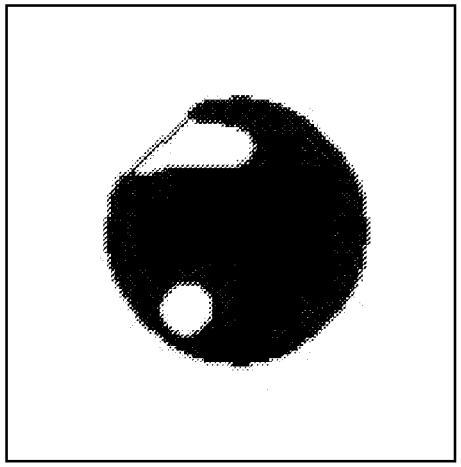
FIG. 14B is an representative image of a convex envelope in a fourth iteration the embodiment reflected in FIG. 10.
Figure 14D:
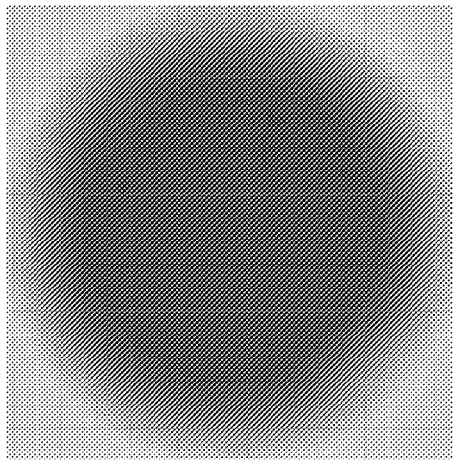
FIG. 14D is an image representative the accumulation obtained in a fourth iteration of the embodiment reflected in FIG. 10.
Figure 14A:
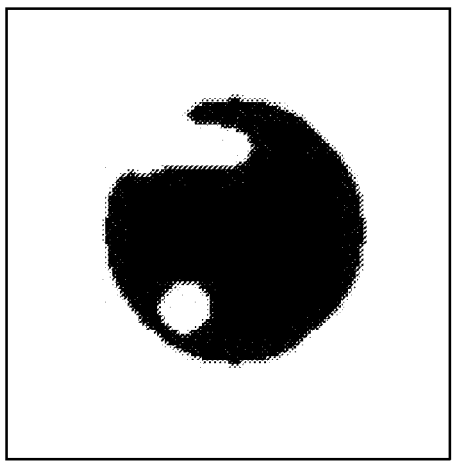
FIG. 14A is an representative image resulting from the thresholding step in a fourth iteration of the embodiment reflected in FIG. 10.
Figure 14C:
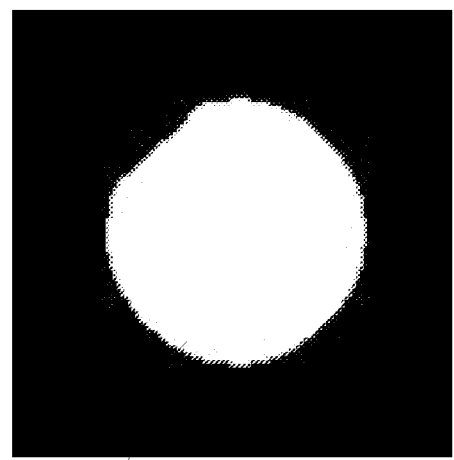
FIG. 14C is an image representative of inner blobs obtained in a fourth iteration of the embodiment reflected in FIG. 10.

FIG. 10 illustrates the main steps in an alternative embodiment of the method. Steps 1020-1050 are identical to steps 520-550 of FIG. 5. The embodiments differ starting at step 1060.

In step 560 of the embodiment of FIG. 5, all void pixels (white pixels) within the estimated non-voided solder ball object were identified. In the alternative embodiment of FIG. 10, at step 1060, all the pixels (white or black) within the estimated non-voided solder ball object (again, determined using the convex envelope or by fitting a pre-defined geometric shape, for example) are identified. As explained previously, the estimated non-voided solder ball object estimates the result of binarizing, at the current value of the binarization threshold variable, a grayscale X-ray image of a version of the solder ball in which the voids are absent. The pixels identified at step 1060 for different iterations of the loop are indicated with reference numerals 1130, 1230, 1330, and 1430 in FIGS. 11C, 12C, 13C, and 14C, respectively.

At step 1070, for each of the identified pixels, the corresponding accumulator in the accumulator array is incremented. In this embodiment, the accumulator array does not accumulate void pixels over different binarization threshold values, but accumulates all pixels of the estimated non-voided solder ball object over different binarization threshold levels. Again, the accumulator array can be viewed as an accumulator image. FIGS. 11D, 12D, 13D, and 14D illustrate the accumulator image obtained at step 1070 for the different iterations of the loop.

At step 1080, once all the binarization threshold values have been processed, the accumulator image provides an approximation of a grayscale X-ray image of a non-voided version of the solder ball.

At step 1095, the accumulator image is subtracted from the original grayscale X-ray image of the solder ball. The result is a void accumulator image similar to that obtained in the previous embodiment once all the binarization threshold values have been processed.

In some embodiments, at step 1095 the accumulator image may be subtracted from a modified version of the original grayscale X-ray image in which the grayscale intensity of all pixels not within the boundary of the solder ball is set to 0, i.e., are set to black.

In this embodiment, if the step size ΔT is equal to 1, all grayscale intensity values found within the boundary of the solder ball in the original X-ray image of the solder ball will be selected as a binarization threshold level. If the step size ΔT is not equal to 1, before subtracting the accumulator image from the grayscale image of the solder ball at step 1185, the grayscale intensities in the grayscale image of the solder ball may be quantized according to the step size ΔT, and/or the grayscale intensities in the accumulator image may be scaled (e.g., multiplied by 3 for a step size of 3).

In addition, in this embodiment, prior to subtracting the accumulator image from the grayscale image of the solder ball at step 1095, a grayscale intensity offset equal to the minimum grayscale intensity value found within the boundary of the solder ball in the original X-ray image (and equal to Tmin) may either be added to the accumulator image or subtracted from grayscale image of the solder ball.

At step 1098, the void accumulator array or image is analyzed to detect the voids and, optionally, characterize the voids, as described above in connection with the embodiment of FIG. 5.

In the embodiments described with reference to FIGS. 5 and 10, the difference in grayscale intensity between any two consecutive binarization threshold values was constant over the set of binarization threshold values. In other embodiments, however, the difference in grayscale intensity between consecutive binarization threshold values may vary over the set of binarization threshold values. An advantage of this is that more binarization threshold values can be selected in ranges of binarization threshold values that are more likely to provide significant void information, and fewer binarization threshold values can be selected in the remaining ranges.

Also, in the embodiments described with reference to FIGS. 5 and 10, the value by which an accumulator is incremented at steps 570 and 1070 was constant over the set of binarization threshold values. In other embodiments, however, each binarization threshold value may be assigned an increment amount (e.g., by means of a look-up table, a parameterized function, etc.) and, at steps 570 and 1070, the accumulator may be incremented according to the assigned increment amount of the respective binarization threshold value. In one embodiment, the increment amount assigned to a particular binarization threshold value may be equal to the difference in grayscale intensity between the particular binarization threshold value and the previous or subsequent binarization threshold value in the set of binarization threshold values. In another embodiment, the increment amount may be based on a relationship between a grayscale intensity in the grayscale X-ray image and an effective thickness of the solder ball.

As noted above, the inventive methods may be employed in a number of applications other than the detection of voids in solder balls.

Some embodiments, for example, may be used in the analysis of solder components or elements other than solder balls or spheres, including solder bumps and/or wafer bumps. In one particular application, these methods may be used in the inspection of "flip chips," assemblies resulting from a method of mounting integrated circuits or other semiconductor devices without the use of wire bonds such as those indicated by reference numeral 50 in FIG. 1. The method may also be applied in the context of the detection of irregularities in a solder used to join pieces of material.

In other embodiments, the methods described above may be used to detect the presence or absence of defects other than voids, including, in particular, the presence or absence of foreign bodies or impurities in a sample. Other embodiments may be employed to detect the presence or absence of things other than defects, such as, for example, the presence or absence of desirable structures.

In other embodiments, the methods disclosed herein may be used to inspect articles or materials other than solder for the presence or absence of desirable or undesirable structures or characteristics. In one embodiment, for example, these methods may be employed to inspect X-ray images of fruits or vegetables for the presence or absence of seeds.

In still further embodiments, the methods described above may be employed to analyze images other than X-ray images, including grayscale or color images of any desired resolution or depth. In some embodiments, for example, the methods may be employed to analyze range data images to locate one or more features of interest.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for the detection of a defect in a solder element based on an X-ray image of the solder element, the method comprising the steps of
    acquiring an X-ray image of the solder element obtained by directing X-rays through the solder element for collection by an X-ray detector;
    binarizing the X-ray image at a plurality of binarization thresholds to obtain a plurality of binarized images, each having a respective binarization threshold;
    for each of the binarized images, extracting information from the binarized image;
    combining the information extracted from each of the binarized images; and
    detecting the defect based on the combined information,
    wherein the step of extracting information from the binarized image comprises the step of estimating the non-defective solder element resulting from the binarization, at the respective binarization threshold, of an X-ray image of a version of the solder element in which the defect is absent.

2. The method of claim 1, wherein the step of extracting information from the binarized image further comprises the step of
    identifying pixels corresponding to the defect within the estimated non-defective solder element.

3. The method of claim 1, wherein the step of extracting information from the binarized image further comprises the step of
    identifying all pixels within the estimated solder element, and
    wherein the step of detecting the defect based on the combined information comprises the step of subtracting the combined information from the X-ray image.

4. The method of claim 1, wherein the step of estimating the non-defective solder element comprises the steps of
    identifying a defective solder element in the binarized image, and
    determining the convex envelope of the identified defective solder element.

5. The method of claim 1, wherein the step of estimating the non-defective solder element comprises the steps of
    identifying a defective solder element in the binarized image, and
    fitting a pre-defined geometric shape to the identified defective solder element.

6. The method of claim 5, wherein the pre-defined geometric shape is an ellipse.

7. The method of claim 5, wherein the pre-defined geometric shape is a circle.

8. The method of claim 1, wherein the defect comprises a void.

9. The method of claim 1, wherein the solder element is a solder ball.

10. The method of claim 1, wherein the step of extracting information from the binarized image comprises the step of
    extracting information corresponding to the defect from the binarized image.

11. A method for the detection of a defect in a solder element based on an X-ray image of the solder element, the method comprising the steps of
    acquiring an X-ray image of the solder element obtained by directing X-rays through the solder element for collection by an X-ray detector;
    binarizing the X-ray image at a plurality of binarization thresholds to obtain a plurality of binarized images, each having a respective binarization threshold;
    for each of the binarized images, extracting information from the binarized image;
    combining the information extracted from each of the binarized images; and
    detecting the defect based on the combined information,
    wherein the X-ray image and each of the binarized images comprise a set of pixels and each pixel in the X-ray image has a corresponding pixel in each of the binarized images, further comprising the step of assigning each set of corresponding pixels in the X-ray image and the binarized images an accumulator;

wherein the step of extracting information from the binarized image comprises identifying pixels in the binarized image that satisfy pre-determined criteria, and wherein the step of combining the information extracted from each of the binarized images comprises, for each of the identified pixels in each of the binarized images, incrementing the accumulator corresponding to the identified pixel.

12. The method of claim 11, further comprising the steps of:

assigning each binarization threshold an increment amount, and incrementing the accumulator according to the increment amount of the respective binarization threshold.

13. The method of claim 12, further comprising the step of assigning each binarization threshold an increment amount based on a relationship between an intensity in the X-ray image and the thickness of the solder element.

14. The method of claim 12, further comprising the step of assigning an increment amount to a binarization threshold based on a difference between the binarization threshold and at least one of a previous and subsequent binarization threshold.

15. The method of claim 11, wherein the defect comprises a void.

16. The method of claim 11, wherein the solder element is a solder ball.

17. The method of claim 11, wherein the step of extracting information from the binarized image comprises the step of extracting information corresponding to the defect from the binarized image.

18. A method for the detection of an irregularity in an object based on an image of the object, the method comprising the steps of:

acquiring an image of the object obtained by an image acquisition device;

binarizing the image at a plurality of binarization thresholds to obtain a plurality of binarized images, each having a respective binarization threshold;

for each of the binarized images, extracting information from the binarized image by estimating the regular object resulting from the binarization, at the respective binarization threshold, of an image of a version of the object in which the irregularity is absent;

combining the information extracted from each of the binarized images; and detecting the irregularity based on the combined information.

19. The method of claim 18, wherein the image of the object is a grayscale image.

20. The method of claim 19, wherein the grayscale image is a range data image.

21. The method of claim 19, wherein the grayscale image is a grayscale X-ray image.

22. The method of claim 18, wherein the object is one of a fruit or vegetable.

23. The method of claim 18, wherein the object is a soldered component.

24. The method of claim 18, further comprising the step of estimating the regular object using a geometric property of the regular object.

25. The method of claim 24, wherein the geometric property is convexity.

26. The method of claim 24, wherein the geometric property is a dimension.

27. The method of claim 24, wherein the geometric property is a shape.

\* \* \* \* \*